United States Patent [19]

Lazarian

[11] Patent Number: 4,899,737
[45] Date of Patent: Feb. 13, 1990

[54] SPLINT FOR COMPLETE CIRCUMFERENTIAL IMMOBILIZATION OF AN EXTREMITY OR A TERMINAL MEMBER OF AN EXTREMITY

[76] Inventor: Vartan J. Lazarian, 47 So. Country Rd., Bellport, N.Y. 11713

[21] Appl. No.: 244,161

[22] Filed: Sep. 14, 1988

[51] Int. Cl.⁴ ................................................ A61F 5/04
[52] U.S. Cl. .................... 128/87 A; 128/880; 2/21
[58] Field of Search ................. 2/21, 163; 128/26, 77, 128/87 R, 87 A, 85, 153

[56] References Cited

U.S. PATENT DOCUMENTS

| | | | |
|---|---|---|---|
| 1,684,076 | 9/1928 | Smith | 128/87 A |
| 1,837,691 | 12/1931 | Thigpen | 128/87 A |
| 2,528,456 | 10/1950 | Stevenson | 128/87 A |
| 2,633,126 | 3/1953 | Newmark | 2/21 |
| 3,039,460 | 6/1962 | Chandler | 128/87 A |
| 3,348,541 | 10/1967 | Loebeck | 2/21 |
| 3,358,682 | 12/1967 | Preston | 128/157 |
| 3,467,379 | 9/1969 | Kistner | 128/87 R |
| 4,644,941 | 2/1987 | Ogle, II | 128/77 |

Primary Examiner—Robert A. Hafer
Assistant Examiner—Charles H. Sam
Attorney, Agent, or Firm—Michael I. Kroll

[57] ABSTRACT

The splint of our invention comprises a substantially cylindrical flexible outer member, an inner liner, advantageously a soft material for comfort, and a plurality of stiffening members interposed between the outer member and the inner liner distributed substantially uniformly about the entire circumference of the terminal member or extremity to provide a uniform pressure around the circumference preventing bending. The stiffening members are not completely rigid, advantageously somewhat flexible steel rods, while the flexible outer member can be a piece of rubber tubing.

6 Claims, 1 Drawing Sheet

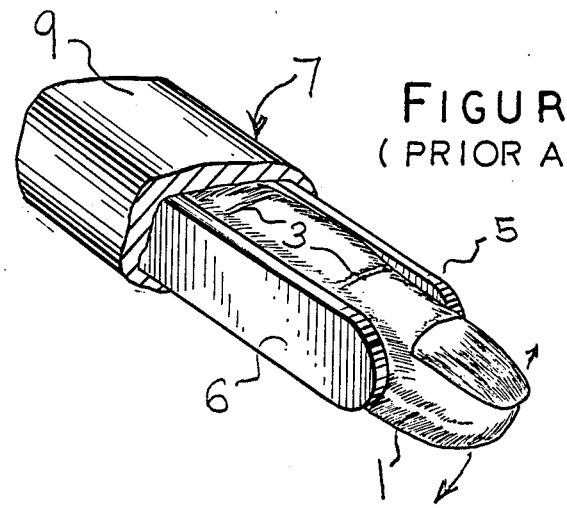
FIGURE 1
(PRIOR ART)
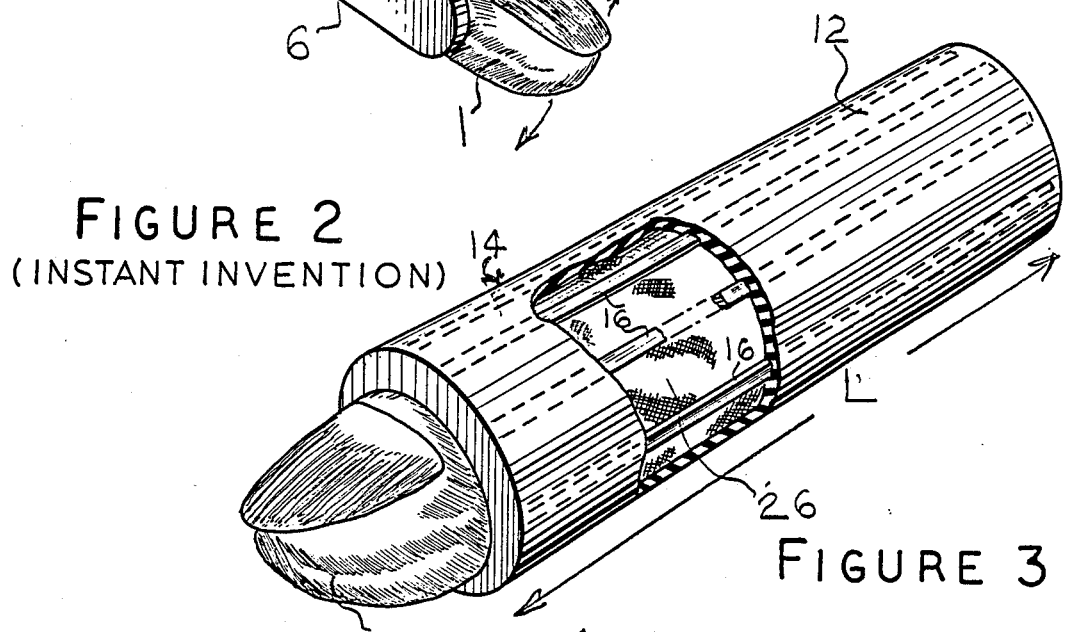
FIGURE 2
(INSTANT INVENTION)
FIGURE 3
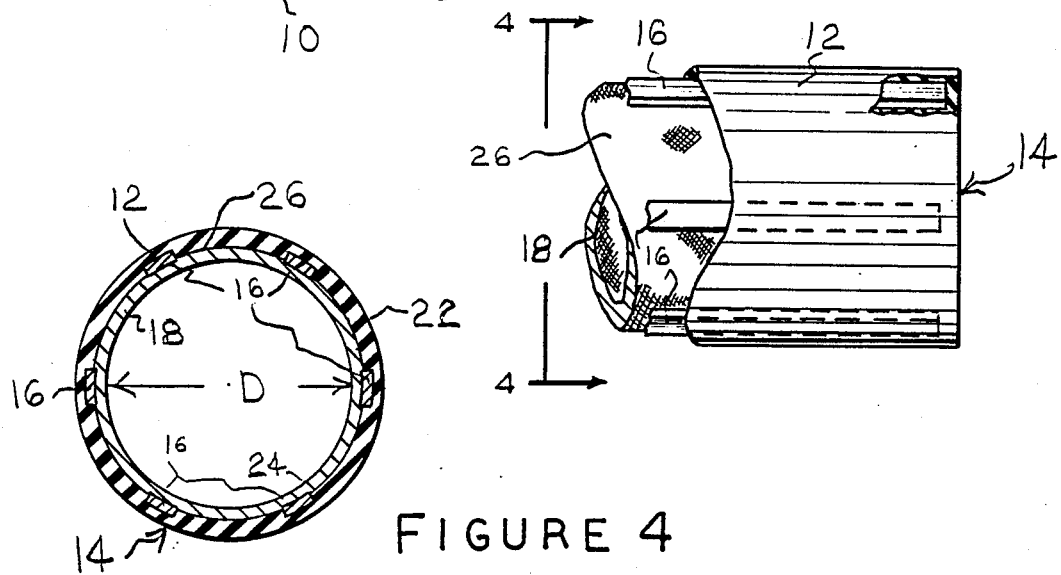
FIGURE 4

SPLINT FOR COMPLETE CIRCUMFERENTIAL IMMOBILIZATION OF AN EXTREMITY OR A TERMINAL MEMBER OF AN EXTREMITY

FIELD OF THE INVENTION

Our invention relates to a device for immobilizing an extremity or a terminal member of an extremity such as a toe or finger for medical purposes.

BACKGROUND OF THE INVENTION

When a finger or toe is fractured or dislocated it is often necessary to immobilize it after restoring the position of the bone to its original position to allow it to heal. This can be done with the aid of device called a splint. By a "splint" we mean here any device which is used to immobilize an extremity of the body or a terminal member of an extremity to allow it to heal or for any other medical purpose.

The known splint comprises several rigid members, usually two flat pieces of wood, which are applied to opposite sides of the finger or toe which is being set after a fracture, and a strip of substantially inelastic cloth or bandage which is wrapped around the finger or toe to hold the rigid members in place. The bandage or strip of cloth can be secured by an adhesive strip, it can have an adhesive-bearing surface or it can be secured by a clip or some other method.

The known splint has several disadvantages. First it is generally substantially inelastic so that it does not allow for changes in anatomy or for swelling leading to discomfort and possible healing problems. Second by itself it is not waterproof or dust-proof so that water, dirt or disease-causing germs can lodge in gaps and crevices between the parts of the splint and the finger or toe. If the splinted terminal member of an extremity or the extremity is frequently washed, the materials making up the splint may swell or weaken. Furthermore if only two pieces of wood are used to provide a rigid support for the finger or toe the splint can be incorrectly applied so that the finger or toe can bend or flex after application. Also if the break is severe supporting two sides of the terminal member of an extremity may not provide enough support for a safe healing process to be guaranteed. Lastly the current splints are not easily removed and replaced by the patient.

It is an object of our invention to provide an improved splint which fixes and supports an extremity or a terminal member of an extremity such as a finger or toe around its entire circumference so that it is kept substantially straight and can not be bent in any direction.

It is also an object of our invention to provide an improved splint which fixes and supports a finger, toe or similar extremity so that it can not be bent in any direction without effecting other parts of the body.

It is an additional object of our invention to provide an improved splint which fixes and supports an extremity or terminal member of an extremity so that it can not bend in any direction but which on the other hand is sufficiently elastic to allow for changes in anatomy and for swelling.

It is another object of our invention to provide an improved splint which fixes and supports an extremity or terminal member of an extremity around its entire circumference, which is completely closed and thus waterproof and does not collect dirt or germs.

It is a further object of our invention to provide an improved splint which fixes and supports an extremity or terminal member of an extremity around its entire circumference but which can be easily removed and replaced by the patient.

It is yet another object of our invention to provide an improved splint which fixes and supports an extremity or a terminal member of an extremity such as a finger or a toe so that the finger or toe can not be bent in any direction but which easily folds up for storage and which does not have an expiration date beyond which it can not be used.

SUMMARY OF THE INVENTION

According to our invention the splint for medical purposes including fixing and supporting extremities or terminal members of extremities of the body comprises a substantially cylindrical elastic outer member, a plurality of stiffening members located inside the elastic outer member and a liner located inside said elastic outer member and the stiffening members, advantageously coextensive with the outer member, to substantially prevent bending or flexing the extremity or the terminal member of the extremity in any direction.

The stiffening members must be stiff enough to substantially prevent bending of the extremity or the terminal member but together with the outer member must also be flexible enough to allow for swelling and changes in anatomy. Application of the instant splint to an extremity does not impair the movement or useage of those parts of the body which are not splinted but completely fixes and supports the extremity or terminal member of the extremity about its entire circumference so that it can not be bent or flexed in any direction.

In one example of our invention the stiffening members between the elastic outer member and the inner liner are distributed uniformly about the circumference to provide a uniform pressure on the extremity or terminal member about the entire circumference.

The substantially cylindrical elastic outer member can be waterproof and grips the finger or toe providing some support. Additional but not complete rigidity is provided by the stiffening members, advantageously metal rods, between the outer member and the liner. The liner is advantageously a soft cotton material chosen for comfort. The outer member should be elastic enough to be easily removed and replaced.

A rubber tubing made from the same rubber used for surgical gloves can be used for the elastic outer member. The stiffening members can be somewhat flexible steel rods but could also have a different cross sectional geometry. Six is a particularly good choice for the number of stiffening members. Additionally the splint may be applied in either direction making it very easy to use.

The splint of our invention is easily folded up for storage and comes in a single piece so that its parts can not be lost and so that there can be no errors in applying the splint to the extremity and the device may be used for sprains, strains etc.

There are no parts of the splint which have a limited shelf-life so that there is no expiration date which sets a time beyond which the splint must be disposed of or not used for medical purposes.

BRIEF DESCRIPTION OF THE DRAWING FIGURES

The above and other objects, features and advantages of the present invention will become more readily apparent from the following specific description, reference being made to the accompanying drawing in which:

FIG. 1 is a perspective view showing a typical prior art splint incorrectly applied to a finger;

FIG. 2 is a partially cutaway perspective view of the instant invention applied to a finger showing the various parts of the splint;

FIG. 3 is a cutaway side view of the splint shown in FIG. 2; and

FIG. 4 is a cross sectional view of the splint shown in FIG. 2 taken along the section line 4—4 of FIG. 3.

DETAILED DESCRIPTION OF THE INVENTION

FIG. 1 shows a typical prior art splint 7 applied to a terminal member 1 of an extremity (a hand of which only the finger is shown) to assist in healing a fracture or dislocation. This splint 7 comprises two flat pieces of wood 5,6 held in place on opposite sides of the finger 1 by a tightly-wound bandage 9. The bandage 9 as usual is comparatively inelastic so that the splint 7 will not give if the terminal member 1 swells. In this case the splint 7 has not been correctly applied as can happen with the splint of the prior art since the joints 3 of the terminal member 1 (the finger) allow the finger to flex in the direction of the arrow. Only a bending motion in the direction of the flat pieces of wood 5,6 is prevented. Certainly the finger is not prevented from bending or flexing about its entire circumference. If the splint 7 were correctly applied, the pieces of wood 5,6 would be rotated through a right angle but bending of the finger would still not be prevented about its entire circumference, especially if one or more joints or bones were broken.

The splint 14 shown in FIGS. 2 to 4 is one example of a splint according to our invention. This splint is shown applied to a finger 10 and it comprises a substantially cylindrical outer member 12, a plurality of rod-like stiffening members 16 located inside the outer member 12 extending longitudinally over the entire length L of the splint 14 and a liner 18 which is positioned inside the outer member 12 and the stiffening members 16. The substantially cylindrical outer member 12 must be made of a material which is elastic enough to fit the extremity and tight enough to provide some support. The stiffening members 16 located inside the outer member 12 are not completely rigid but are stiff enough to provide support and to hold the extremity or terminal member of the extremity together with the outer member 12 fixed in position preventing bending or flexing in any direction about its entire circumference. The liner 18 is advantageously made of a soft material such as cotton chosen for comfort.

As shown in FIG. 4 the stiffening members 16, which in this example are steel rods, are advantageously distributed uniformly around the circumference of the splint 14. Thus a uniform pressure is applied at all points around the circumference of the splint 14 when it is applied. The outer surface 26 of the liner 18 bears the stiffening members 16 which do not contact the finger 10. The inner surface 22 of the elastic outer member 12 contacts the outer surface 26 of the soft liner 18 except where the stiffening members 16 are interposed between them. The stiffening members 16 may be rigidly attached to the outer member 12 and/or the liner 18 by adhesive, stitching or other means. The inner surface 24 of the soft liner 18 contacts the extremity 10 and thus must be of a material which does not irritate the skin, i.e. cotton.

The substantially cylindrical outer member 12 may be an elastic rubber tubing made from the same rubber used for surgical gloves for example. Thus the splint 14 is waterproof, dust-proof and closed completely when applied. Since it is elastic it allows for swelling and is easily removed and replaced by the patient.

The splint 14 has an inner diameter D and a length L which are chosen to fit the size of the terminal member to which it is applied. Thus the splint 14 of our invention must be manufactured with a variety of diameters and lengths to fit different individuals and extremities.

The number of stiffening members 16 used in this particular example is 6 but any number of stiffening members may be used in our invention. Furthermore the stiffening members 16 need not be rod-like but can be flat or can have a square cross section.

It will be understood that each of the elements described above, or two or more together, may also find a useful application in other devices differing from the type of device described above.

The invention is not intended to be limited to the details provided above and it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of the prior art, fairly constitute essential characteristics of the generic or specific aspects of the invention.

What is claimed is new and what is desired to be protected by Letters Patent is set forth in the following claims:

1. A splint, for a broken terminal member of an extremity or for an extremity, comprising:
   (a) a substantially cylindrical elastic outer member free of "O" rings and flaps so that pain is not intensified, said cylindrical elastic outer member open at both ends so that it can expand from the nail bed past the first joint of the finger so that the tip of the finger including the nail is visible and not restrictive throughout the healing process;
   (b) a substantially cylindrical liner inside said outer member, open at both ends and
   (c) a plurality of stiffening members positioned inside said outer member and each being independent of each other and formed as an integral unit between said liner and said outer member, said stiffening members being stiff enough to substantially prevent bending of said extremity or said terminal member but together with said outer member are flexible enough to allow for swelling and changes in anatomy.

2. A splint according to claim 1 wherein said stiffening members are distributed uniformly about the circumference of said extremity or terminal member to provide a uniform pressure about said circumference.

3. A splint according to claim 1 wherein six of said stiffening members are provided and each of said stiffening members is a somewhat flexible steel rod disposed totally independently of each other.

4. A splint according to claim 1 wherein said elastic outer member comprises an elastic rubber tubing made from the same rubber used for surgical gloves.

5. A splint according to claim 1 wherein said substantially cylindrical liner is substantially coextensive with said outer member and is made of a soft material.

6. A splint according to claim 5 wherein said soft material comprises cotton.

* * * * *